(12) United States Patent
Venkatesh et al.

(10) Patent No.: US 6,475,510 B1
(45) Date of Patent: Nov. 5, 2002

(54) PROCESS FOR MANUFACTURING BITE-DISPERSION TABLETS

(75) Inventors: Gopadi M. Venkatesh, King of Prussia, PA (US); Nageswara R. Palepu, Harlow (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/581,334

(22) PCT Filed: Dec. 17, 1998

(86) PCT No.: PCT/US98/27061

§ 371 (c)(1),
(2), (4) Date: Jun. 8, 2000

(87) PCT Pub. No.: WO99/32092

PCT Pub. Date: Jul. 1, 1999

Related U.S. Application Data

(60) Provisional application No. 60/168,258, filed on Dec. 19, 1997.

(51) Int. Cl.[7] .................................................. A61K 9/20

(52) U.S. Cl. ........................ 424/441; 424/464; 424/465; 514/772.3; 514/778; 514/779; 514/781; 514/783; 514/784; 514/785; 514/786

(58) Field of Search ................................. 424/464, 465, 424/441

(56) References Cited

U.S. PATENT DOCUMENTS

| | | |
|---|---|---|
| 5,861,172 A | 1/1999 | Martin et al. ................ 424/464 |
| 5,869,095 A | 2/1999 | Gergely et al. ............. 424/466 |

*Primary Examiner*—James M. Spear
(74) *Attorney, Agent, or Firm*—Dara L. Dinner; Stephen Venetianer; Charles M. Kinzig

(57) ABSTRACT

This invention relates to a method for the manufacture of Bite-dispersion tablets which disperse easily and quickly in the oral cavity, after a gentle bite, without the aid of water, and if necessary includes masking the bitter taste of medicaments. The process comprises preparing a dry granulation of one or more of medicaments blended with suitable excipients, flavors and a combination of a waxy material and phospholipid (BMI-60) or an intense sweetener derived from fruit flavonoids (Neohesperidine) for taste-masking and compressing into tablets which can be packaged in bottles or blisters using conventional equipment.

101 Claims, No Drawings

PROCESS FOR MANUFACTURING BITE-DISPERSION TABLETS

This application is the § 371 national stage entry of PCT/US98/27061, filed Dec. 17, 1998, and which claims the benefit of provisional application Ser. No. 60/168,258, filed Dec. 19, 1997.

FIELD OF THE INVENTION

The present invention relates to method of manufacture of bite-dispersion (fast dispersible) tablets containing taste masked medicaments for oral administration without water.

BACKGROUND OF THE INVENTION

Tablets of medicaments developed for the treatment of a variety of diseases are the most preferred dosage forms based on the ease of administration and patient compliance. However, most of medicaments are bitter tasting, and persons orally taking these medications experience some discomfort or pain. In order to avoid this bitter taste, medicaments are therefore swallowed. However, infants and the elderly both experience some difficulty in swallowing. Thus, we are confronted with two problems—suppression of bitter taste and the rapid disintegration of tablets in the oral cavity in order to avoid the difficulty of swallowing.

The following methods have been used for taste masking of pharmaceuticals, viz., addition of sweetener or flavors, microencapsulation and coating of medicaments with materials, generally polymers, soluble in stomach. U.S. Pat. No. 5,260,072 discloses a method of making chewable tablets of taste-masked medicaments, whereby the taste masking is achieved by rotogranulating the active material with a binder and carrier material and coating the rotogranulations with a taste masking polymer blend of cellulose acetate, or cellulose acetate butyrate and polyvinyl pyrrolidone. Alternative approaches of the prior art (U.S. Pat. No. 5,084,278) include microencapsulating the tablet core containing bitter actives with polymers such as ethyl cellulose, methamethacrylate copolymers. Medicament absorbates with complex silicates such as magnesium aluminum silicate, magnesium trisilicate or cation exchange resin have also been proposed U.S. Pat. No. 3,085,942, 3,140,978, 4,711,774 and 5,219,563 and WO 96/39126).

WO 96/23494 discloses a taste masking method by wet granulating the active medicament, a silicate adsorbate, and a weak base such as calcium carbonate, which acts as a dissociation agent and compressing the granulation into tablets. U.S. Pat No. 5,275,823 teaches a method of preparing chewable tablets containing unpleasant tasting medicaments such as cimetidine by coating cimetidine with Eudragit E 100 and incorporating certain hygroscopic water-insoluble substances such as Al/Mg antacids as external excipients. The major drawback of these above noted methods is that the tablets still need to be swallowed and complete release of the active medicament may take up to 2 hours depending on the polymer system used therein.

Japanese Patent No. 55-8966 and 62-265234 disclose addition of lecithin (phosphatidylcholine) and cephalin singly, or in combination with lecithin. Japanese Patent No. 55-108254 proposes the use of an absorbent material. U.S. Pat. No. 5,407,921 discloses a method for suppressing the bitter taste by adding an acidic phospholipid or an acidic lyso-phospholipid. Bitter substances are commonly hydrophobic and it is believed that hydrophobic interactions with the receptor sites lead to their binding. Y. Katsuragi and coworkers [Pharm. Research Vol. 12, 658–662, 1995; Nature, 365:213–214, 1993; Brain Research, 713, 240–245, 1996; Biochimica et Biophysica Acta, 1289, 322–328, 1996] disclose the use of lipoproteins, PA-LG or PA-LA composed of phosphatidic acid (PA) and β-lactogloblin (LG) and PA and (α-lactalbumin, respectively. These lipoproteins being hydrophobic, reversibly suppress the responses of the target sites for bitter substances. U.S. Pat. No. 5,407,921 discloses addition of acidic phospholipid or lysophospholipid for suppressing the bitter taste. These methods have been found, by themselves, to be insufficient to give the desired suppression of the bitter taste of certain pharmaceuticals.

Technologies for producing tablets which rapidly disintegrate in the oral cavity have also been described in the literature. These include immediate disintegrating tablets (WOWTAB®) of Yamanouchi Pharmaceuticals Company of Japan fast-dissolving tablets (WO 95/33446) of Proctor & Gamble Company; Lyoc® from Laboratoire Farmalyoc; fast dissolving taste masked OraSolv tablets from Cima Labs Inc.; FlashTab tablets of Programpharm; fast dissolving lyophilized dosage forms in blisters (Zydis®) from RP Scherrer; and the rapidly dissolving tablets of Fuisz Technologies all of which involve laborious manufacturing processes. Further, these tablets need to be packed in special packages.

The WOWTAB technology, noted above (Japanese Patents Nos. 6-010112, 6-086652, 6-0616) comprises coating a pharmaceutically active ingredient and mannitol/lactose with maltose, initially crystalline changing to an amorphous state, and then granulating. These granules are compressed into porous tablets at very low compression forces. When subjected to high humidity, maltose absorbs moisture to recrystallize, therefore the residual moisture in the formulation is removed prior to packaging. The tablets of hardness of 3–5 kP thus obtained, were found to require special packaging to avoid attrition during storage/transport.

The technology described in Proctor & Gambles WO 95/33446 patent application comprises forming a nonrupturable drug matrix by first dissolving/dispersing in water a taste masking agent such as xanthan gum, methylmethacrylate copolymer etc. and a pharmaceutically active agent and then driving off the moisture and blending with an orally acceptable carrier (effervescent) such as sodium bicarbonate and compressing into tablets. Moisture and heat sensitive actives cannot be processed, and the process is a time consuming and expensive one.

The flash dispersal technology of Cima relies on compressing into soft friable tablets blends of an effervescent couple and commercially available microencapsulated medicaments. The process is thus a complicated and expensive one which also requires stringent environmental controls (<20° C./10% relative humidity and tablet hardness ~1–2.5 kP) and also specialized packaging.

The Lyoc technology involves freeze drying a suspension of a medicament and excipients into pre-formed blisters. This technology is obviously not suitable for most active ingredients. Furthermore, the technology requires specialized equipment and is expensive.

FlashTab is a flash dispersal system which involves coating a drug with a Eudragit polymer (methylmethacrylate copolymer) to provide rapid release of the drug in the stomach, and formulating this microencapsulated drug with an effervescent couple to produce a flash dispersal tablet. The microencapsulation system currently uses an undesirable solvent based manufacturing process, and the cost of goods is high.

U.S. Pat. No. 5,407,921 describes a method of suppressing the bitter taste of materials to be placed in the oral cavity, such as foods, drinks and medicaments.

The process described in WO 94/08576 (Glaxo Group Limited) consists of first encapsulating ranitidine or a suitable salt form in polymer matrix such as ethylcellulose or using molten waxy material such as Carnauba wax, glyceryl tristearate or tripalmitate (high molecular weight straight chain saturated or unsaturated fatty acids, esters and alcohols) to obtain substantially tasteless ranitidine granules with a drug content of about 20% w/w, granulating said granules with xylitol, flavor, etc. and compressing into chewable tablets or dispersing in molten triglyceride suppository base and theobroma oil and preparing tablet shaped moulds. In either case, the process is laborious and expensive.

A need exists for a cost effective, rapid operation process for producing tablets containing medicaments, which provide for ease of oral administration (fast disintegration in the mouth without water) and taste-masking of any bitter ingredients.

SUMMARY OF THE INVENTION

The present invention is to a fast dispersing tablet, also referred to as a bite-dispersable tablet, containing an active ingredient. The pharmaceutically acceptable fast-dispersing tablet formulation of the present invention has a structure comprising compacted granulates; these granulates comprises a medicament together with a combination of a waxy material and an intense sweetner and/or a taste-masking agent, a pharmaceutically acceptable excipent selected from xylitol, mannitol, maltodextrin, or sorbitol, or a combination thereof; and optionally a flavoring agent and disintegrant; the granulates being compacted together into a tablet form together with extragranular components which are a disintegrant, a sweetner and/or taste-masking agent, and a pharmaceutically acceptable excipient selected from xylitol, mannitol, maltodextrin, or sorbitol, or a combination thereof Another aspect of the present invention is a process for the preparation of fast dispersing, or bite-dispersing tablets for oral administration, which process comprises:

A. Manufacturing taste-masked granules:
  (i) admixing at least one pharmaceutically active ingredient, with one or more pharmaceutically acceptable excipients selected from the group consisting of a xylitol, directly compressible mannitol, maltodextrin or sorbitol; a waxy material; an intense sweetener or taste-masking agent; and optionally a disintegrant and a flavoring agent; and
  (ii) preparing the admixture of step (i) for compression by dry granulation [such as via slugging or roller compacting], milling and sieving; and B. Manufacturing Bite-dispersion tablets
  (iii) blending the product of step (ii) with additional pharmaceutically acceptable excipients which comprise xylitol, mannitol, maltodextrin or sorbitol; and optionally includes a flavoring agent, a sweetener/taste-masking agent, and a disintegrant; and
  (iv) compressing the mixture of step (iii) into tablets.

DETAILED DESCRIPTION OF THE INVENTION

In accordance with the present invention, a process is disclosed herein for the manufacturing of bite-dispersible tablets containing one or more medicaments, or active ingredients/agents, which will disperse easily, and quickly, after a gentle bite when taken orally.

It has now been found that by properly selecting a combination of commonly used excipients, such as xylitol and directly compressible mannitol, maltodextrin or sorbitol, preparing dry granules thereof, and subsequently blending these granules with additional excipients, in an extragranular admixture, a bite-dispersible tablet can be produced which rapidly disintegrates in the oral cavity without water. It will be recognized by the skilled artisan that the proportions of the above noted excipients may need to be "fine tuned" for each medicament, or combination of medicament, such as those disclosed herein.

The process herein comprises:
(1) blending intragranular components together which include, one or more medicaments (also referred to herein as active agents or active ingredients), individually or in combination, together with any suitable or desired excipients, and a combination of a waxy material and a taste-masking agent, which may include an intense sweetener, preferably BMI-60 or Neohesperidine; and optionally may include one or more additional flavoring agents and a disintegrant; and
(2) preparing a dry granulation mixture by techniques well known in the art, such as by roller compacting or slugging, milling and sieving as may be required; and
(3) preparing a compression mix by blending the intragranular dry granules from step (2) with any necessary or desired extragranular excipients as will be described herein; and
(4) compressing the mixture from step (3) into tablets.

The resulting tablets have been found to have a low friability, so that they can be readily packaged into bottles or blisters using conventional equipment.

The desired fraction of the dry granulation mixture, produced in step 2 above, may optionally be heat treated (Thermal Infusion Process, TIPped) following procedures well known in the art, such as those described in U.S. Pat. No. 5,690,959 prior to blending with additional excipients and compressing into tablets.

Steps # 1 and 2 above provide for substantially taste-masked granules of a medicament, while Steps # 3 and 4 result in the desired bite-dispersible tablet. In an alternative embodiment of the present invention, instead of the taste-masked granules produced in Step # 2, commercially available taste-masked granules of medicaments, such as polymer coated granules from Eurand America or microencapsulated Descote® granules, or any other suitable polymer coated medicament, may instead be blended with the excipients and flavors and compressed into bite-dispersion tablets following Steps # 3 and 4.

It is recognized that there are many suitable means for producing taste-masked intragranular medicaments for use in the intragranular component mix. Often the polymer coated granules, or microencapsulated granules of the active ingredients, may be active agents which have a bitter, or unpleasant taste. These medicaments may be coated, for instance, with separate layers of polymers, such as methacrylate ester copolymers, as taught in U.S. Pat. No. 5,578, 316. Suitable coating materials described in this application include a wide range of copolymers, such as those available under the tradename of Eudragit. These copolymers are manufactured and marketed by Röhm Pharma of Darmstadt, Germany.

It is recognized that these polymeric aqueous dispersions may also contain additives such as, plasticizers, pigments, talc and the like, which may be included for use herein in the intragranular mix. These additives include plasticizers are employed to assist in the film forming characteristics of the polymeric coating and also to provide greater integrity and elasticity to the films coat. Exemplary of plasticizers that may be employed in the coatings of this invention are triethyl citrate, triacetin, tributyl citrate, acetyl triethyl citrate, acetyl tributyl citrate, dibutyl phthalate, dibutyl sebacate, vinyl pyrrolidone and propylene glycol. The amount of plasticizer present in the aqueous dispersion may be from 5% to about 30% by weight of the dry polymers.

Suitably the desired excipients for use in the intragranular admixture of process step (i) above include, but are not limited to, xylitol, directly compressible mannitol, maltodextrin or sorbitol; or a combination thereof, preferably xylitol. However, the extragranular mixture requires the use of certain pharmaceutically acceptable excipients, and these excipients may be selected from xylitol, directly compressible mannitol, maltodextrin or sorbitol; or a combination thereof, preferably xylitol.

The present invention does require in the intragranular mixture, a component which is a waxy material, and a second component which is either an intense sweetener, such as those derived from fruit flavonoids, or a taste masking agent such as the lipoproteins and phospholipids derived from soy lecithin, which are further described herein. As noted above, the admixture may optionally comprise additionally flavoring agents, and a distintegrent. If, however, the intragranular mixture uses a polymer coated granule of a pharmaceutically active agent, or a commercially available taste-masked granule of a pharmaceutically active ingredient is used instead, it is recognized that the waxy material and the second component are not necessary and may therefore be optionally included.

Suitable waxy materials for use herein include, but are not limited to, the mono-, di- or tri- $C_{10-30}$ aliphatic esters of glycerol, preferably glycerol palmito-stearate or glyceryl behenate; the high molecular weight ($C_{10-30}$) straight chain aliphatic alcohols, such as stearyl alcohol or cetyl alcohol; and mixtures of high molecular weight aliphatic acids and esters; or combinations thereof Preferably, the waxy material is stearyl alcohol or cetyl alcohol, or is glycerol palmito-stearate or glyceryl behenate.

Suitable taste-masking agents which may be incorporated in the intragranular formulation preferably include the lipoproteins and phospholipids derived from soy lecithin, such as BMI-60, a fractionated product from soy lecithin from Kao Corporation. However, other suitable components for taste-masking of active ingredients include, but are not limited to, synthetic or naturally occurring waxes such as Compritol® or Precirol® (glyceryl behenate or glycerol palmito-stearate, from Gattefosse s.a., France), cetyl alcohol or carnauba wax. It is noted that the waxy material and the taste-masking agents may be the same agents for use in the intragranular admixture, such as in the case of use of the synthetic or naturally occurring waxes noted above; or may be a combination thereof Suitable sweetener agents for use in the intragranular formulation preferably include the intense sweeteners derived from fruit flavonoids, such as Neohesperidine DC from EM Industries, Inc. Suitably the required second component in the intragranular admixture may be either be the above noted taste-masking agent, the intense sweetner or a combination thereof Preferably the second component is either BMI-60 or Neohesperidine DC, a combination of these two products.

Suitably, the waxy material, in combination with BMI-60 or Neohesperidine DC, is present at a level of from about 1% to about 30%, preferably from about 3% to about 20% by weight of composition. In the intragranular admixture if the first and second component are present it is preferably from about 0.5 to about 2% w/w of the formulation. Alternatively, the waxy material to the taste-masking/sweetener ratio will vary in these formulations from about 20:1 to about 5:1 (total formulation).

The waxy material, taste-masking agents and sweetener agents noted herein for use in the intragranular component mix may also be optionally used in the extragranular admixture.

Suitable active ingredients for incorporation into the bite-dispersion tablets of the present invention include the many bitter, unpleasant tasting, or numbing effects of drugs which include, but are not limited to, histamine $H_2$-antagonists, such as, cimetidine, ranitidine, famotidine, nizatidine, etinidine; lupitidine, nifenidine, niperotidine, roxatidine, sulfotidine, tuvatidine and zaltidine; antibiotics, such as penicillin, ampicillin, amoxycillin, and erythromycin; acetaminophen; aspirin; caffeine, dextromethorphan, diphenhydramine, bromopheniramine, chloropheniramine, theophylline, spironolactone, NSAIDS's such as ibuprofen, ketoprofen, naprosyn, and nabumetone; 5HT4 inhibitors, such as granisetron, or ondansetron; seratonin re-uptake inhibitors, such as paroxetine, fluoxetine, and sertraline; vitamins such as ascorbic acid, vitamin A, and vitamin D; dietary minerals and nutrients, such as calcium carbonate, calcium lactate, etc., or combinations thereof.

The above drugs are not limiting but merely exemplary of unpleasant tasting drugs that may be employed in this invention. Additionally, other compounds such as the nonsteriodal anti-inflammatory drugs (NSAIDs), such as naprosyn, i.e. the propionic acid derivatives, are a preferred embodiment of this invention. Suitably, these agents, in particular the anti-inflammatory agents, may also be combined with other active therapeutic agents, such as various steroids, decongestants, antihistamines, etc., as may be appropriate.

The inactive ingredients or excipients, optionally used in the intragranular admixture and the required extragranular admixtures, include the pharmaceutically acceptable excipients such as xylitol [a sweetening agent (2.5 times as sweet as mannitol) with a large negative heat of solution—153 J/g)], fructose, sorbitol (heat of solution:—111 J/g), mannitol (heat of solution:—121 J/g), and maltodextrin.

Suitable flavoring agents for use herein include, but are not limited to, wintergreen, orange, grapefruit, and cherry-raspberry. If the intragranular mixture does not contain a polymer coated active ingredient than preferably the mixture includes a flavouring agent. Further, if a flavouring agent is present in the extragranular mix it should be present from about 0.5 to about 3% w/w of the total tablet formulation.

The formulation may optionally contain suitable disintegrants (both intra and extra-granular) such as, but not limited to, sodium starch glycolate [Explotab®], crosslinked polyvinylpyrrolidone [Crospovidone b®], corn starch, acacia, Croscarmellose of sodium [Ac-di-sol®], sodium carboxymethylcellulose, veegum, alginates. Preferably the disintegrant is sodium starch glycolate, or corn starch.

While a disintegrant is an optional component in the intragranular mix, it is preferably corn starch or acacia, with the drug to disintegrant ratio of about 50:1 to 20:1.

While a disintegrant is also an optional component in the extragranular mix, it is preferably sodium starch glycolate (Explotab), Croscarmellose of sodium (Ac-Di-Sol) or crosslinked polyvinylpyrrolidone (Crospovidone), and is present in about 1–4% wt. of formulation.

The formulation may also optionally contain suitable lubricants, (both intra and extra-granular) such as but not limited to, magnesium stearate, stearic acid and its pharmaceutically acceptable alkali metal salts, calcium stearate, sodium stearate, Cab-O-Sil, Syloid, sodium lauryl sulfate, sodium chloride, magnesium lauryl sulfate or talc. Preferably, a suitable lubricant is magnesium stearate or stearic acid. The amount of lubricant present in the total formulation may be from about 0.5 to about 2.0 by weight of composition. Suitably, the lubricant is present in the extra-granular mix.

In addition to these above noted excipients, the formulation may also contain high surface area ingredients such as talc, acacia, corn starch, magnesium trisilicate or magnesium aluminum silicate. Suitably, the high surface area materials are present at a level from about 1% to about 10% by weight of composition, preferably from about 2% to about 6% by weight of composition.

The formulation may also include coloring agents, or pigments, such as FD&C or D&C approved lakes and dyes, iron oxide and titanium dioxide. The amount of pigment present may be from about 0.1% to about 2.0% by weight of the composition.

The formulation may also contain suitable lubricants in the intra and extra-granular mixtures, such as but not limited to, magnesium stearate or stearic acid. Suitably, the lubricant is present in the extra-granular mix.

Additional other conventional pharmaceutical diluents or excipients may be also be included, as needed, in either the intragranular or extragranular admixture. Suitable excipients which may be employed include, for example, fillers, binders, lubricants, binders, compression aids, and wetting agents. To further assist patient compliance, the formulation may also contain sweeteners such as aspartame, sodium cyclamate and sodium saccharinate; and flavorants such as those noted above.

The present invention provides for a method of manufacturing bite-dispersion tablets which are capable of rapid operation, is cost effective, and suitable particularly to moisture/heat sensitive medicaments.

Another aspect of this invention, as compared to other fast-dispersion technologies, is that no specialized manufacturing or packaging equipment is required to manufacture these tablets.

Suitably, the tablets of the present invention include:

a) 1–60 parts of at least one medicament; and b) 10–90 parts, preferably 15–85 parts of xylitol; and c) 0.5–20 parts, preferably 1.0–20 parts of a waxy material, such as glyceryl behenate (Compritol®), or glycerol palmitostearate (Precirol®); and d) optionally, 0.5–7 parts, more preferably 1.0–4.0 parts of an intense sweetener/taste masking agent such as Neohesperidine or BMI-60 (the actual range depending upon the bitterness of the medicament).

The xylitol content in the formulations may vary significantly depending on the medicament; for example, 1 part of Granisetron hydrochloride to 90 parts of xylitol, preferably to 40–70 parts of xylitol, depending on the required dose; 1 part of Paroxetine hydrochloride to 15 parts of xylitol, preferably to 4–10 parts of xylitol; 1 part of Acetaminophen to 6 parts of xylitol, preferably to 2–4 parts of xylitol; 1 part of Ibuprofen to 6 parts of xylitol, preferably to 2–4 parts of xylitol; 1 part of Cimetidine free base to 6 parts of xylitol, preferably to 2–4 parts of xylitol; 5 parts of Calcium Carbonate to 1 part of xylitol, preferably 2 parts of Calcium Carbonate to 3–2 parts of xylitol; per total weight of formulation. Preferably, parts are ratios determined by w/w % of the total formulation.

The medicament, waxy material and sweetener/taste masking agent are blended together with suitable additional excipients, preferably roller compacted and milled, to produce palatable granules, this admixture is also referred to herein as the intragranular component. These intragranular components, or for instance, commercially available microencapsulated granules of the medicament, are then blended with additional excipients including xylitol, flavors and a lubricant (also referred to herein as the extragranular components) and compressed into fast dispersing tablets.

The taste-masked drug granule to xylitol ratio in the extragranular component of the tablet formula varies from about 1:10 to 3:1, preferably from about 1:5 to 2:1, depending on the strength of the dosage form and/or the extent of bitterness associated with the medicament.

The drug to xylitol ratio, if present, in the intragranular component of the tablet formula varies from about 1:30 to 10:1, preferably from about 1:20 to 3:1, depending on the strength of the dosage form and/or the extent of bitterness associated with the medicament.

The drug to waxy material (if present) in the intragranular composition varies from about 10:1 to 1:30, preferably from about 5:1 to 1:20, depending on the dose and bitterness of the medicament. The ratio of the taste-masked granule (steps #1 and 2) to xylitol in the extragranular mix varies from about 1:10 to 3:1, preferably from about 4:1 to 1:1.

Another aspect of the present invention is the novel formulation for a fast-dispersing pharmaceutical tablet for oral administration which tablet has a structure comprising compacted granulates; the granulates comprising a medicament together with a combination of a waxy material and a taste-masking agent, optionally with an intense sweetner, and/or flavoring agent; and optionally a pharmaceutically acceptable excipient selected from xylitol, mannitol, maltodextrin, or sorbitol, or a combination thereof, the granulates being compacted together into a tablet form together with extragranular components which are a disintegrant, a sweetner and/or taste-masking agent, and a pharmaceutically acceptable excipient selected from xylitol, mannitol, maltodextrin, or sorbitol, or a combination thereof Preferably, the medicament in the tablet as noted above, is an analgesic, antacid, antiemetic, anti-inflammatory agent, arthritis medication, calcium supplement, antihistamine, decongestant, or a mixture thereof.

Preferably, the tablet granulates further comprise an intragranular pharmaceutically acceptable excipiewhich is xylitol, and an extragranular granular excipient is xylitol.

Preferably the granulates include an intense sweetener which is derived from fruit flavonoids; or a taste masking agent of a lipoprotein or acidic phospholipids derived from soy lecithin. More preferably, the phospholipid is derived from a fractionated product derived from soy lecithin.

Preferably, the granulate waxy material comprises a synthetic or naturally occurring wax, or a mono-, di- or tri- $C_{10}$–$C_{30}$ aliphatic ester of glycerol, such as glycerol palmito-stearate or glyceryl behenate. Or the waxy material may comprise a high molecular weight (C10–C30) straight chain aliphatic alcohol, or mixtures of high molecular weight aliphatic acids and esters, such as stearyl alcohol or cetyl alcohol.

Preferably, the waxy material is in combination with BMI-60 or Neohesperidine DC and is present at a level of from about 1% to about 30%, preferably from about 3% to about 20% by weight of composition.

The granulates may further comprise a high surface area material comprising acacia or corn starch, or a combination thereof, at a level of from about 1% to about 10%, preferably from about 2% to about 6% by weight of composition. Preferably, the tablets may also comprise a high surface area material comprising acacia or corn starch, or a combination thereof, at a level of from about 1% to about 10% in the extragranular component of the formulation, preferably wherein the high surface area material is acacia.

The granulates may further comprises a flavoring agent, or the extragranular component may further comprises a flavoring agent, or a combination thereof In the process of making the tablets preferably, the granualtes are optionally subjected to heat treatment prior to being compacted with the extragranular components.

Examples of Bite-Dispersion Tablet Formulations

The examples of typical Bite-dispersion tablet formulations are illustrated in the following sections. These examples are neither exhaustive nor limited in their scope.

EXAMPLE 1

Blend 80 g of granisetron.HCl with 68 g of xylitol, 4 g of Neohespiridine and 8 g of Compritol (glyceryl behenate) and mill the blend using a micropulverizer. Prepare the following dry granulation formulation by blending:

Intragranular Admixture

| Ingredient | % W/W |
| --- | --- |
| Milled Granisetron blend | 11.2 |
| Xylitol | 71.0 |
| Maltodextrin | 15.0 |
| Flavoring agent | 1.0 |
| Aspartame (sweetener) | 0.2 |
| Compritol ™ (glyceryl behenate) | 1.6 |

Roller compact, mill and sieve to produce #30–80 mesh granules. Prepare the following compression mix and compress tablets of 1.0 mg (granisetron free base) tablets to weigh 100 mg and of hardness of 1–2 kP:

| Ingredient | % W/W |
| --- | --- |
| Sieved granules | 20.0 |
| Xylitol | 64.6 |
| Maltodextrin | 10.0 |
| Sodium starch glycolate | 3.0 |
| Flavoring agent | 0.5 |
| Aspartame | 0.3 |
| Compritol ™ | 1.6 |
| Total | 100.0 |

The tablets thus produced were found to disperse easily in the mouth with a cool feel, after a gentle bite. These tablets conformed to the UPS content uniformity requirements and also, exhibited excellent friability (0.3% in 3 min. or 75 revolutions) requiring no special packaging for transportation and distribution.

EXAMPLE 2

Prepare the following roller compactor blend formulation:

Intragranular Admixture

| Ingredient | % W/W |
| --- | --- |
| Paroxetine.HCl | 50.0 |
| Xylitol | 21.5 |
| Flavoring agent | 1.0 |
| BMI-60 (phospho-lipid) | 1.5 |
| Aspartame | 1.0 |
| Precirol ™ (glycerol palmitostearate) | 25.0 |
| Total | 100.0 |

Roller compact the blend, mill and sieve to produce #30–80 mesh granules and heat treat at 45–48° C. for 15 min. Prepare the following compression mix and compress into 30 mg strength Bite-Dispersion tablets weighing 200 mg:

| Ingredient | % W/W |
| --- | --- |
| Treated granules | 38.1 |
| Xylitol | 39.1 |
| Spray dried Mannitol | 13.8 |
| Acacia | 5.0 |
| Flavoring agent | 1.0 |
| BMI-60 | 1.0 |
| Aspartame | 1.0 |
| Compritol ™ | 1.0 |
| Total | 100.0 |

The taste masked tablets thus produced rapidly disperse in the mouth with a cool feel, after a gentle bite. The tablets having a hardness of 1–3 kP and an acceptable friability do not require special packaging for transportation.

EXAMPLE 3

Prepare the following roller compactor blend formulation:.

Intragranular Admixture:

| Ingredient | % W/W |
| --- | --- |
| Acetaminophen | 60.0 |
| Xylitol | 11.5 |
| Flavoring agent | 1.0 |
| BMI-60 (phospho-lipid) | 1.5 |
| Aspartame | 1.0 |
| Precirol ™ | 25.0 |
| Total | 100.0 |

Roller compact the blend, mill and sieve to produce #40–80 mesh granules and heat treat at 45–48° C. for 15 min. Prepare the following compression mix and compress into 80 mg strength Bite-Dispersion tablets weighing 350 mg:

| Ingredient | % W/W |
|---|---|
| Treated granules | 38.1 |
| Xylitol | 39.1 |
| Spray dried Mannitol | 12.0 |
| Corn starch | 5.0 |
| Ac-Di-Sol (Croscarmellose sodium) | 1.8 |
| Flavoring agent | 1.0 |
| BMI-60 | 1.0 |
| Aspartame | 1.0 |
| Precirol ™ | 1.0 |
| Total | 100.0 |

The taste masked tablets thus produced rapidly disperse in the mouth with a cool feel, after a gentle bite. The tablets having a hardness of 1–3 kP and an acceptable friability (0.4% in 3 min.) do not require special packaging for transportation.

EXAMPLE 4

Weigh ingredients, screen excipients, and prepare the following compaction mix for roller compacting:
Intragranular Admixture

| Ingredient | % W/W |
|---|---|
| Cimetidine free base | 55.0 |
| Xylitol | 14.5 |
| Orange flavor | 2.0 |
| BMI-60 | 2.0 |
| Precirol ™ | 25.0 |
| Aspartame | 0.5 |
| Peppermint flavor | 1.0 |
| Total | 100.0 |

Weigh ingredients, screen excipients, and prepare the following compression mix and compress the intragranular admixture with the compression (extragranular admixture) into 200 mg strength Bite-Dispersion cimetidine tablets weighing 750 mg.
Extragranular admixture:

| Ingredient | % W/W |
|---|---|
| Sieved Granules | 48.5 |
| Xylitol | 31.8 |
| SD Mannitol | 9.1 |
| BMI-60 | 1.0 |
| Corn Starch | 5.0 |
| Ac-Di-Sol | 1.8 |
| Aspartame | 0.5 |
| Peppermint flavor | 1.5 |
| Compritol ™ | 0.8 |
| Total | 100.0 |

The taste masked tablets thus produced rapidly disperse in the mouth with a cool feel, after a gentle bite. The tablets having a hardness of 2–3 kP and an acceptable friability (0.5% in 3 min.) do not require special packaging for transportation.

EXAMPLE 5

Weigh ingredients, screen excipients, and prepare the following compression mix and compress into 250 mg strength Bite-Dispersion acetaminophen tablets weighing 800 mg:
Intragranular Admixture:

| Ingredient | % W/W |
|---|---|
| Descote Granules* | 52.1 |
| Xylitol | 26.0 |
| SD Mannitol | 12.1 |
| BMI-60 | 2.0 |
| Corn Starch | 3.0 |
| Ac-Di-Sol | 1.8 |
| Aspartame | 0.5 |
| Flavoring agent | 1.7 |
| Compritol ™ | 0.8 |
| Total | 100.0 |

*Taste-masked Descote ® 60% acetaminophen granules manufactured by Particle Dynamics, St. Louis, MO 63144.

The taste masked tablets thus produced rapidly disperse in the mouth with a cool feel, after a gentle bite. The tablets having a hardness of 2–3 kP and an acceptable friability (0.5% in 3 min.) do not require special packaging for transportation.

EXAMPLE 6

Weigh ingredients, screen excipients, and prepare the following compaction mix for roller compacting:
Intragranular Admixture:

| Ingredients | W/W (%) |
|---|---|
| Calcium carbonate | 70.0 |
| Xylitol | 16.0 |
| Precirol ™ | 10.0 |
| BMI-60 | 1.5 |
| Aspartame | 1.0 |
| Flavoring Agent | 1.5 |
| Total | 100.0 |

Roller compact the blend, mill and sieve to produce #30–80 mesh granules. Prepare the following compression mix and compress into 500 mg strength Bite-Dispersion tablets weighing 1.1 g:

| Ingredient | % W/W |
|---|---|
| Sieved Granules | 64.9 |
| Xylitol | 16.2 |
| SD Mannitol | 9.1 |
| BMI-60 | 2.0 |
| Corn Starch | 3.0 |
| Ac-Di-Sol | 1.8 |
| Aspartame | 0.5 |
| Flavoring Agent | 1.7 |
| Compritol ™ | 0.8 |
| Total | 100.0 |

The taste masked tablets thus produced rapidly disperse in the mouth with a cool feel, after a gentle bite. The tablets having a hardness of 2–3 kP and an acceptable friability (0.5% in 3 min.) do not require special packaging for transportation.

EXAMPLE 7

In an example of the alternative embodiment using pre-tasted masked granules, the following example is prepared. The ingredients are weighed, screen excipients, and prepare the following compression mix and compress into 250 mg strength Bite-Dispersion ibuprofen tablets weighing 1.0 g:

| Ingredients | W/W (%) |
|---|---|
| Cimetidine Granules* | 35.7 |
| Xylitol | 40.2 |
| SD Mannitol | 11.5 |
| BMI-60 | 2.0 |
| Corn Starch | 5.0 |
| Ac-Di-Sol | 1.8 |
| Aspartame | 1.0 |
| Flavoring agent | 2.0 |
| Compritol ™ | 0.8 |
| Total | 100.0 |

*Taste-masked Microcap ® 60% cimetidine granules manufactured by Eurand America, Vandalia, Ohio.

The taste masked tablets thus produced rapidly disperse in the mouth with a cool feel, after a gentle bite. The tablets having a hardness of 2–3 kP and an acceptable friability (1.2% in 3 min.) do not require special packaging for transportation.

EXAMPLE 8

Prepararation of the following formulation may be made using a roller compactor:
Intragranular Admixture

| Ingredient | % W/W |
|---|---|
| Paroxetine.HCl | 80.0 |
| Xylitol | 11.0 |
| Flavoring agent | 2.0 |
| BMI-60 (phospho-lipid) | 2.0 |
| Aspartame | 1.0 |
| Precirol (glycerol palmitostearate) | 4.0 |
| Total | 100.0 |

Roller compact the blend, mill and sieve to produce #30–80 mesh granules. These sieved granules are coated in a fluid bed granulator/particle coater with a solution of Eudragit polymer, E100 dissolved in a mixture of ethyl alcohol and purified water. Prepare the following compression mix and compress into 30 mg strength Bite-Dispersion tablets weighing 125.0 mg:

| Ingredient | % W/W |
|---|---|
| Treated granules | 38.1 |
| Xylitol | 39.1 |
| Spray dried Mannitol | 13.8 |
| Acacia | 5.0 |
| Flavoring agent | 1.0 |
| BMI-60 | 1.0 |
| Aspartame | 1.0 |
| Compritol | 1.0 |
| Total | 100.0 |

The taste masked tablets thus produced rapidly disperse in the mouth with a cool feel, after a gentle bite. The tablets having a hardness of 1–3 kP and an acceptable friability do not require special packaging for transportation.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A process for the preparation of a fast dispersing tablet for oral administration, which process comprises:

(i) admixing together intragranular components which are at least one pharmaceutically active ingredient, one or more pharmaceutically acceptable excipients which are xylitol, directly compressible mannitol, maltodextrin and sorbital, or a combination thereof; a waxy material which is a synthetic or natural wax, a mono-, di- or tri-($C_{10-30}$) aliphatic esters of glycerol, a ($C_{10-30}$) straight chain aliphatic alcohol, a ($C_{10-30}$) aliphatic acid, and a ($C_{10-30}$) aliphatic ester, or combinations thereof; an intense sweetener or taste-masking agent; and optionally a disintegrant; and (ii) preparing the admixture of step (i) for compression by dry granulation, slugging, roller compacting, milling or sieving, or combinations thereof; and (iii) blending the product of step (ii) with an extragranular component which comprises a pharmaceutically acceptable excipient of xylitol, directly compressible mannitol, maltodextrin or sorbitol, or a combination thereof; and optionally a sweetener or taste-masking agent;

(iv) compressing into tablets.

2. The process according to claim 1 wherein the intragranular pharmaceutically acceptable excipient is xylitol.

3. The process according to claim 1 wherein the extragranular granular excipient is xylitol.

4. The process according to claim 1 wherein the pharmaceutically active ingredient is an antidepressant, analgesic, antacid, antiemetic, anti-inflammatory agent, arthritis medication, calcium supplement, antihistamine, a decongestant, seratonin reuptake inhibitor, or a $5HT_4$ inhibitor, or a mixture thereof.

5. The process according to claim 1 wherein the intragranular sweetener is derived from fruit flavonoids.

6. The process according to claim 1 wherein the intragranular taste masking agent is a lipoprotein or acidic phospholipid derived from soy lecithin.

7. The process according to claim 6 wherein the phospholipid is derived from a fractionated product derived from soy lecithin.

8. The process according to claim 1 wherein the waxy material comprises a synthetic or naturally occurring wax, or a mono-, di- or tri-$C_{10}$–$C_{30}$ aliphatic ester of glycerol.

9. The process according to claim 8 wherein the waxy material is glycerol palmito-stearate or glyceryl behenate.

10. The process according to claim 1 wherein the waxy material comprises a (C10–C30) straight chain aliphatic alcohol, or mixtures of (C10–C30) aliphatic acids and esters.

11. The process according to claim 10 wherein the waxy material is stearyl alcohol or cetyl alcohol.

12. The process according to claim 1 wherein the waxy material is in combination with a fruit flavonoid, or a lipoprotein or acidic phospholipid derived from soy lecithin.

13. The process according to claim 1 wherein the intragranular dry granules are optionally subjected to heat treatment prior to admixture with the extragranular components.

14. The process according to claim 1 or wherein the intragranular dry granules are blended with xylitol as an extragranular excipient and compressed into rapid dispersing tablets.

15. The process according to claim 14 wherein the dry granules are optionally blended with a high surface area material comprising acacia or corn starch, or a combination thereof.

16. The process according to claim 15 wherein the high surface area material is present at a level of from about 1% to about 10% by weight of the composition.

17. The process according to claim 12 wherein the combination is present from about 1% to about 30% by weight of the composition.

18. The process according to claim 15 wherein the high surface area material is acacia.

19. The process according to claim 15 wherein the high surface area is corn starch included in the intragranular mix at a level of from about 1% to about 10% by weight of total composition.

20. The process according to claim 15 wherein the high surface area material is magnesium aluminum silicate or magnesium trisilicate and is from about 1% to about 4% by weight of composition.

21. The process according to claim 1 wherein the intragranular component includes a flavoring agent.

22. The process according to claim 1 wherein the extragranular component includes a flavoring agent.

23. A process for the preparation of fast dispersing tablets for oral administration, which process comprises:
(i) admixing together intragranular components include at least one microencapsulated pharmaceutically active ingredient, one or more pharmaceutically acceptable excipients, a waxy material which is a synthetic or naturally occurring wax, a mono-, di- or tri-$(C_{10-30})$ aliphatic ester of glycerol, a $(C_{10-30})$ straight chain aliphatic alcohol, a $(C_{10-30})$ aliphatic acid, or a $(C_{10-30})$ aliphatic ester, or combinations thereof; and optionally an intense sweetener or taste-masking agent; and a disintegrant;
(ii) preparing the admixture of step (i) for compression by dry granulation, slugging, roller compacting, milling or sieving, or combinations thereof; and
(iii) blending the product of step (ii) with an extragranular component comprising a pharmaceutically acceptable excipient selected from the group consisting of a xylitol, directly compressible mannitol, maltodextrin or sorbitol; and optionally a sweetener/taste-masking agent and a flavoring agent; and
(iv) compressing into tablets.

24. The process according to claim 23 wherein the microencapsulated active ingredient is coated with a polymer which is soluble, swellable, and releases the active ingredient in the stomach.

25. The process according to claim 24 wherein the active ingredient is a propionic acid NSAID, an $H_2$ receptor antagonist or a proton pump inhibitor.

26. The process according to claim 23 wherein the extragranular pharmaceutically acceptable excipient is xylitol.

27. The process according to claim 23 wherein the intragranular admixture includes a taste masking agent which is a lipoprotein or acidic phospholipid derived from soy lecithin.

28. The process according to claim 27 wherein the phospholipid is derived from a fractionated product derived from soy lecithin.

29. The process according to claim 26 wherein the intragranular admixture includes BMI-60.

30. A fast-dispersing pharmaceutical tablet formulation comprising compacted granulates; the intragranular granulates comprising a medicament together with a combination of a waxy material which is a synthetic or naturally occuring wax, a mono-, di- or tri-$C_{10-30}$ aliphatic esters of glycerol, a $(C_{10-30})$ straight chain aliphatic alcohol, a $(C_{10-30})$ aliphatic acid, or a $(C_{10-30})$ aliphatic ester, or combinations thereof and a taste-masking agent or an intense sweetner, optionally with a flavoring agent, and a pharmaceutically acceptable excipent selected from xylitol, mannitol, maltodextrin, or sorbitol, or a combination thereof, the granulates being compacted together into a tablet form together with extragranular components which are a disintegrant, a sweetner and/or taste-masking agent, and a pharmaceutically acceptable excipent selected from xylitol, mannitol, maltodextrin, or sorbitol, or a combination thereof.

31. The tablet formulation according to claim 30 wherein the medicament is an antidepressent, analgesic, antacid, antiemetic, anti-inflammatory agent, arthritis medication, calcium supplement, antihistamine, decongestant, seratonin reuptake inhibitor, or a $5HT_4$ inhibitor, or a mixture thereof.

32. The tablet according to claim 30 wherein the intragranular pharmaceutically acceptable excipient is xylitol.

33. The tablet according to claim 30 wherein the extragranular granular excipient is xylitol.

34. The tablet according to claim 30 wherein the intense sweetener is derived from fruit flavonoids.

35. The tablet according to claim 30 wherein the taste masking agent is a lipoprotein or acidic phospholipid derived from soy lecithin.

36. The tablet according to claim 35 wherein the phospholipid is derived from a fractionated product derived from soy lecithin.

37. The tablet according to claim 30 wherein the waxy material comprises a synthetic or naturally occurring wax, or a mono-, di- or tri-$C_{10}$–$C_{30}$ aliphatic ester of glycerol.

38. The tablet according to claim 37 wherein the waxy material is glycerol palmito-stearate or glyceryl behenate.

39. The tablet according to claim 30 wherein the waxy material comprises a high molecular weight (C10–C30) straight chain aliphatic alcohol, or mixtures of high molecular weight aliphatic acids and esters.

40. The tablet according to claim 39 wherein the waxy material is stearyl alcohol or cetyl alcohol.

41. The tablet according to claim 30 wherein the waxy material is in combination with a fruit flavonoid, or a lipoprotein or acidic phospholipid derived from soy lecithin.

42. The tablet according to claim 30 wherein the granulates are optionally subjected to heat treatment prior to being compacted with the extragranular components.

43. The process according to claim 30 wherein the granulates further comprise a high surface area material comprising acacia or corn starch, or a combination thereof.

44. The tablet according to claim 43 wherein the high surface area material is present at a level of from about 1% to about 10%.

45. The tablet according to claim 30 which further comprises a high surface area material comprising acacia or corn starch, or a combination thereof in the extragranular component of the formulation.

46. The tablet according to claim 45 wherein the high surface area material is acacia.

47. The tablet according to claim 46 wherein the granulate further comprises a flavoring agent.

48. The tablet according to claim 30 wherein the extragranular component further comprises a flavoring agent.

49. A fast-dispersing pharmaceutically acceptable tablet for oral administration comprising:
   a) 1–60 parts of at least one medicament; and
   b) 10–90 parts of xylitol; and
   c) 0.5–20 parts of a waxy material, selected from glyceryl behenate or glycerol palmitostearate; and
   d) optionally, 0.5–7 parts of an intense sweetener and/or taste masking agent.

50. The tablet according to claim 49 wherein the intense sweetener and taste masking agent are derived from a fruit flavonoid, or a lipoprotein or acidic phospholipid derived from soy lecithin.

51. The tablet according to claim 49 wherein the xylitol is present in an amount of 15–85 parts.

52. The tablet according to claim 49 wherein the waxy material is present in an amount of 1.0–20 parts.

53. The tablet according to claim 49 wherein the medicament is an antidepressant, analgesic, antacid, antiemetic, anti-inflammatory agent, arthritis medication, calcium supplement, antihistamine, decongestant, seratonin reuptake inhibitor, or a $5HT_4$ inhibitor, or a mixture thereof.

54. The process according to claim 16 wherein the high surface area material is from about 2% to about 6% by weight of composition.

55. The process according to claim 54, wherein the high surface area material is in the extragranular mixture of the composition.

56. The process according to claim 1 wherein the waxy material and the intense sweetner and taste masking agent, or a combination thereof, are present in a ratio of from about 20:1 to about 5:1.

57. The process according to claim 1 wherein the extragranular component further comprises a disintegrant.

58. The process according to claim 57 wherein the distintegrant is sodium starch glycolate, sodium croscarmellose, or cross-linked polyvinylpyrrolidone.

59. The process according to claim 58 wherein the distintegrant is present from about 1 to about 4% by weight.

60. The process according to claim 1 wherein the intragranular component comprises a distintegrant which is sodium starch glycolate, sodium croscarmellose, cross-linked polyvinylpyrrolidone, sodium carboxymethylcellulose, veegum, corn starch, acacia, or an alginate.

61. The process according to claim 60 wherein the distintegrant is present in a ratio of pharmaceutically active ingredient to distintegrant of about 50:1 to 20:1.

62. The process according to claim 61 wherein the disintegrant is corn starch or acacia.

63. The process according to claim 1 wherein the intragranular component and/or the extragranular component further comprises a lubricant.

64. The process according to claim 60 wherein the lubricant is present from about 0.5 to about 2.0 by weight.

65. The process according to claim 3 wherein the ratio of pharmaceutically actve ingredient to xylitol in the extragranular component of the tablet is from about 1:10 to 3:1.

66. The process according to claim 3 wherein the ratio of pharmaceutically acitve ingredient to xylitol in the intragranular component of the tablet is from about 1:30 to 10:1.

67. The process according to claim 3 wherein the ratio of pharmaceutically acitve ingredient to waxy material in the intragranular component of the tablet is from about 10:1 to 1:30.

68. The process according to claim 1 wherein the extragranular component further comprises a waxy material which is a mono-, di- or tri-$C_{10\text{-}30}$ aliphatic esters of glycerol, a ($C_{10\text{-}30}$) straight chain aliphatic alcohol, a ($C_{10\text{-}30}$) aliphatic acid, a ($C_{10\text{-}30}$) aliphatic ester, or combinations thereof.

69. The process according to claim 68 wherein the waxy material is gylcerol palmitosterate, glycerol beheneate, stearyl alcohol or cetyl alcohol.

70. The process according to claim 1 wherein the extragranular component comprises a sweetener or taste masking agent which is derived from a fruit flavonoid, or is a lipoprotein or acidic phospholipid derived from soy lecithin.

71. The process according to claim 70 wherein the phospholipid is derived from a fractionated product derived from soy lecithin.

72. The process according to claim 55 wherein the combination is present from about 3% to about 20% by weight of the composition.

73. The process according to claim 44 wherein the high surface area material is from about 2% to about 6% by weight of composition.

74. The tablet according to claim 45 wherein the high surface area material is present at a level of from about 1% to about 10%.

75. The tablet according to claim 30 wherein the waxy material and the intense sweetner and taste masking agent, or a combination thereof, are present in a ratio of from about 20:1 to about 5:1.

76. The tablet according to claim 30 wherein the distintegrant is sodium starch glycolate, sodium croscarmellose, or cross-linked polyvinylpyrrolidone.

77. The tablet according to claim 76 wherein the distintegrant is present from about 1 to about 4% by weight.

78. The tablet according to claim 30 wherein the granulate further comprises a distintegrant which is sodium starch glycolate, sodium croscarmellose, cross-linked polyvinylpyrrolidone, sodium carboxymethylcellulose, veegum, corn starch, acacia, or an alginate.

79. The process according to claim 78 wherein the distintegrant is present in a ratio of pharmaceutically active ingredient to distintegrant of about 50:1 to 20:1.

80. The process according to claim 79 wherein the disintegrant is corn starch or acacia.

81. The process according to claim 30 wherein the extragranular component further comprises a waxy material which is a mono-, di- or tri-$C_{10\text{-}30}$ aliphatic esters of glycerol, a ($C_{10\text{-}30}$) straight chain aliphatic alcohol, a ($C_{10\text{-}30}$) aliphatic acid, a ($C_{10\text{-}30}$) aliphatic ester, or combinations thereof.

82. The process according to claim 81 wherein the waxy material is gylcerol palmitosterate, glycerol beheneate, stearyl alcohol or cetyl alcohol.

83. The process according to claim 30 wherein the extragranular component sweetener or taste masking agent is derived from a fruit flavonoid, or is a lipoprotein or acidic phospholipid derived from soy lecithin.

84. The process according to claim 83 wherein the phospholipid is derived from a fractionated product derived from soy lecithin.

85. The tablet according to claim 50 wherein the intense sweetener and/or taste masking agent is Neohesperidine or BMI-60.

86. The process according to claim 23 wherein the waxy material is gylcerol palmitosterate, glycerol beheneate, stearyl alcohol or cetyl alcohol.

87. The process according to claim 23 wherein the intense sweetener is derived from a fruit flavonoid.

88. The process according to claim 23 wherein the extra-granular component sweetener or taste masking agent is derived from a fruit flavonoid, or is a lipoprotein or acidic phospholipid derived from soy lecithin.

89. The process according to claim 88 wherein the phospholipid is derived from a fractionated product derived from soy lecithin.

90. The process according to claim 23 wherein the waxy material and the intense sweetner and taste masking agent, or a combination thereof, are present in a ratio of from about 20:1 to about 5:1.

91. The process according to claim 23 wherein the distintegrant is sodium starch glycolate, sodium croscarmellose, cross-linked polyvinylpyrrolidone, sodium carboxymethylcellulose, veegum, corn starch, acacia, or an alginate.

92. The process according to claim 91 wherein the distintegrant is present in a ratio of pharmaceutically active ingredient to distintegrant of about 50: 1 to 20:1.

93. The process according to claim 92 wherein the disintegrant is corn starch or acacia.

94. The process according to claim 23 wherein the extra-granular component further comprises a distintegrant which is sodium starch glycolate, sodium croscarmellose, or cross-linked polyvinylpyrrolidone.

95. The process according to claim 94 wherein the distintegrant is present from about 1 to about 4% by weight.

96. The process according to claim 23 wherein the intra-granular components further comprise a high surface area material which is acacia or corn starch, or a combination thereof.

97. The process according to claim 96 wherein the high surface area material is present at a level of from about 1% to about 10% by weight of the composition.

98. The process according to claim 97 wherein the high surface area material is present from about 2% to about 6% by weight of composition.

99. The process according to claim 23 wherein the extra-granular component further comprises a high surface area material.

100. The process according to claim 99 wherein the high surface area material is acacia or corn starch which is present from about 1% to about 10% by weight of total composition.

101. The process according to claim 23 wherein the intragranular pharmaceutically acceptable excipient is xylitol, directly compressible mannitol, maltodextrin, or sorbitol or a combination thereof.

* * * * *